United States Patent [19]
Osypka

[11] Patent Number: 5,261,419
[45] Date of Patent: Nov. 16, 1993

[54] CARDIAC PACEMAKER LEAD

[76] Inventor: Peter Osypka, Basler Strasse 109, D-7889 Grenzach-Wyhlen, Fed. Rep. of Germany

[21] Appl. No.: 795,006

[22] Filed: Nov. 15, 1991

[30] Foreign Application Priority Data

Dec. 19, 1990 [EP] European Pat. Off. ............ 90124817

[51] Int. Cl.$^5$ ................................................ A61N 1/05
[52] U.S. Cl. ..................................... 607/122; 607/120
[58] Field of Search ................ 128/784, 785, 786, 642

[56] References Cited

U.S. PATENT DOCUMENTS

| Re. 32,227 | 8/1986 | Dutcher | 128/785 |
|---|---|---|---|
| 4,924,881 | 5/1990 | Brewer | 128/786 |
| 5,003,992 | 4/1991 | Holleman et al. | 128/786 |

FOREIGN PATENT DOCUMENTS

| 0047013 | 3/1982 | European Pat. Off. |
| 0282047 | 9/1988 | European Pat. Off. |
| 0368568 | 5/1990 | European Pat. Off. |
| 2539553 | 3/1977 | Fed. Rep. of Germany |
| 3146182 | 6/1983 | Fed. Rep. of Germany |

Primary Examiner—William E. Kamm
Assistant Examiner—Scott M. Getzow
Attorney, Agent, or Firm—Peter K. Kontler

[57] ABSTRACT

A cardiac pacemaker lead wherein a tubular catheter has a proximal end connected to a pacemaker and a distal end provided with an electrode which can be anchored in or otherwise connected with a wall in the heart of a patient. The lead can be extracted from the body of the patient by resorting to an elongated flexible wire-like stylet having a front end receivable in an internal chamber of the distal end of the catheter. The front end of the stylet constitutes or includes a first coupling element and the chamber confines or is defined by a second coupling element which can be engaged by the first coupling element, e.g., in response to rotation of the fully inserted stylet relative to the catheter or in response to heating of the first coupling element. The coupling prevents tearing of the flexible portion of the catheter and/or separation of the flexible portion from the distal end during extraction of the stylet. The chamber in the distal end of the catheter communicates with a passageway for the stylet, and such passageway is defined by the flexible portion of the catheter.

11 Claims, 4 Drawing Sheets

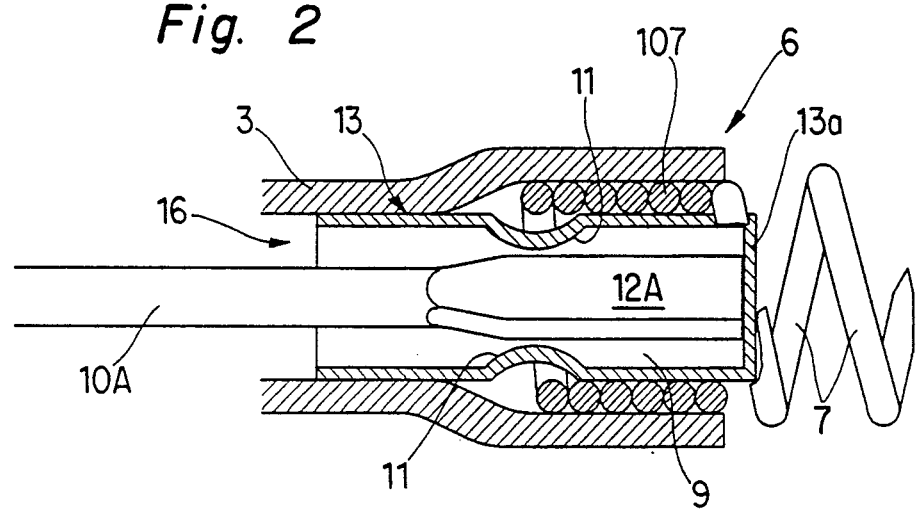
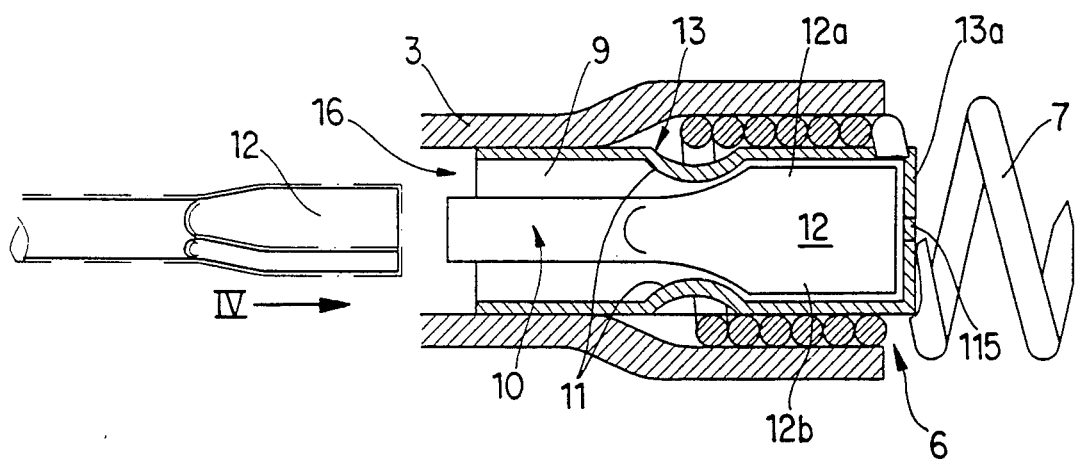
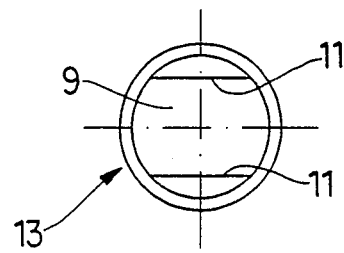

CARDIAC PACEMAKER LEAD

BACKGROUND OF THE INVENTION

The invention relates to improvements in leads which are utilized to connect a cardiac pacemaker with an electrode in the heart, e.g., with a corkscrew-shaped or tip-shaped electrode which is anchored in a wall of a patient's heart. Still more particularly, the invention relates to improvements in cardiac pacemaker leads of the type wherein an elongated flexible catheter carries an electrode at its distal end and defines a passageway for an elongated flexible stylet in the form of a wire or the like.

Cardiac pacemaker leads of presently known design are constructed to implant any one of a variety of different electrodes in the heart of a patient. The electrode can resemble a corkscrew, a so-called tip, an umbrella, a pronged structure or a device having bristle-like projections which serve to anchor the electrode in the tissue of a wall in the heart. Reference may be had, for example, to commonly owned German patent application No. 25 39 553 (published Mar. 10, 1977) which shows a cardiac pacemaker lead with an electrode in the form of a corkscrew. Commonly owned German Pat. No. 31 46 182 (application published Jun. 1, 1983) discloses a lead with a substantially umbrella-like electrode.

Cardiac pacemaker leads of the above outlined character exhibit the advantage that the electrode can be firmly and reliably implanted in the tissue of a wall in the heart of a patient. This is desirable and advantageous in order to ensure predictable stimulation when the pacemaker is in use. However, conventional leads also exhibit a serious drawback, namely that the electrode and the remainder of the lead cannot be readily withdrawn from a patient's body, e.g., after several months or after several years of use when such removal is dictated by infection or for any other reason. Therefore, it is often necessary to resort to open heart surgery with attendant problems involving trauma, danger of infection and extremely high cost.

Heretofore known attempts and proposals to extract a cardiac pacemaker lead without surgery involve the application of a pull to the proximal end of the lead, i.e., to that end which is connected to the pacemaker and is readily or reasonably readily accessible to a physician. A drawback of such proposal is that the lead is likely to break or tear since the major part of the lead normally consists of convoluted wire which is often surrounded by an insulating sheath of plastic material. Neither the coiled wire nor the sheath is capable of standing tensional stresses of a magnitude which is necessary to extract a properly implanted cardiac pacemaker lead several months or years after implantation.

In order to reduce the likelihood of breakage or tearing of a standard cardiac pacemaker lead, additional proposals include the provision or utilization of rollers or weights which are affixed to the proximal end of the lead and remain affixed for a period of several days to ensure gradual extraction of the electrode and distal end of the lead from the heart of a patient. Such mode of extracting the electrode and the entire lead is a hit-and-miss proposition so that it is normally, or at least often, followed by surgery. Moreover, the application of a constant pull for an extended period of time can result in separation of the distal end from the remaining major portion of the implanted lead so that the removal of the distal end necessitates an open heart surgery.

European patent application No. 0 47 013 of Stokes (published Mar. 10, 1982) discloses a body implantable lead which is designed to deliver stimulation energy to a heart or another body site. The distal end or head of the lead is provided with rearwardly inclined tines which ensure reliable anchoring of the head into the tissue. This lead exhibits the same drawbacks as the aforediscussed leads.

European patent application No. 0 368 568 of Goode et al. (published May 16, 1990) discloses a heart lead removal apparatus. The apparatus employs a stylet with an expandable member which is inserted in the coiled structure of the lead. A drawback of such proposal is that the exertion of a pull upon the coiled structure can result in separation of the coiled structure from the distal end of the lead.

European patent application No. 0 282 047 of Bisping (published Sep. 14, 1988) discloses a flexible lead wherein a coil spring in the distal end is caused to store energy which can be dissipated for the purpose of withdrawing a corkscrew-shaped electrode from body tissue. Such dissipation of energy is initiated in response to axial displacement of a piston in the distal end of the lead.

OBJECTS OF THE INVENTION

An object of the invention is to provide a cardiac pacemaker lead which can be more readily extracted from the body of a patient than heretofore known leads.

Another object of the invention is to provide a lead which can be manipulated to ensure reliable engagement of an electrode with a selected portion of the body of a patient and to ensure rapid, effortless and highly predictable extraction of the distal end of the lead and of the electrode from the body.

A further object of the invention is to provide a novel and improved catheter for use in the above outlined cardiac pacemaker lead.

An additional object of the invention is to provide a novel and improved stylet for use in the above outlined lead.

Still another object of the invention is to provide a novel and improved distal end for the catheter in the above outlined cardiac pacemaker lead.

A further object of the invention is to provide a novel and improved method of manipulating the stylet for the purpose of engaging the electrode with tissue in the selected part of a patient's body and/or for the purpose of ensuring predictable extraction of the distal end of the catheter and its electrode from the body.

An additional object of the invention is to provide a lead which exhibits all advantages of heretofore known (reliably implantable) leads and is designed in such a way that the danger of breakage of its catheter during extraction of the catheter and electrode from a patient's body is negligible or nil.

Another object of the invention is to provide a lead wherein the catheter is less likely to break and the connection between the tubular portion of the catheter and its distal end or head is less likely to become separated than in heretofore known leads.

A further object of the invention is to provide a combination of a cardiac pacemaker and a lead which exhibits the above outlined advantages.

An additional object of the invention is to provide novel and improved means for coupling a stylet to the catheter of a cardiac pacemaker lead.

SUMMARY OF THE INVENTION

The invention is embodied in a lead which can be used to connect a cardiac pacemaker with a wall of a heart. The improved lead comprises an elongated flexible tubular catheter having a distal end including an electrode which is engageable with the wall upon implantation of the distal end into the heart. The catheter has a chamber at the distal end and defines an elongated passageway which communicates with the chamber, and the lead further comprises means for extracting the distal end and its electrode from the heart. The extracting means comprises an elongated flexible stylet having a front or distal end which is insertable into the chamber through the passageway of the catheter, and an engageable coupling including a first coupling element which is provided in the catheter at (e.g., in) the chamber and a second coupling element which is provided on the stylet at the front end of the stylet and is engageable with the first coupling element upon insertion of the front end of the stylet into the chamber. The electrode can include a corkscrew or it can constitute or include a so-called tip electrode.

The catheter has a proximal end and the passageway has an inlet which is provided at the proximal end of the catheter to permit insertion of the front end of the stylet.

In accordance with one presently preferred embodiment of the coupling, one of the coupling elements comprises at least one projection and the other coupling element can comprise a socket for the at least one projection. The stylet is preferably rotatable in the passageway of the catheter between at least one first angular position in which the second coupling element can bypass the first coupling element during insertion of the front end of the stylet into the chamber, and a second angular position in which the second coupling element is at least partially aligned with the first coupling element to extract the distal end of the catheter from the heart in response to application to the stylet of a pull in a direction to extract the front end of the stylet from the chamber. The at least one projection can be disposed in the chamber. For example, the distal end of the catheter can comprise a housing which surrounds the chamber and has at least one depressed portion which extends into the chamber and constitutes the at least one projection.

In accordance with another presently preferred embodiment of the coupling, the second coupling element contains or consists of memory metal and is deformable in response to temperature changes upon insertion of the front end of the stylet into the chamber to thereby engage the first coupling element. The latter can include an annular shoulder in the chamber. Such lead preferably further comprises means for changing the temperature of the second coupling element, and such temperature changing means can include a source of electrical energy outside of the catheter. The stylet then comprises or constitutes a conductor which connects the energy source with the second coupling element so that the latter can be caused to change its temperature and to thus engage the first coupling element upon completed insertion of front end of the stylet into the chamber.

In accordance with a further presently preferred embodiment of the coupling, the coupling elements are provided with threads. For example, the first coupling element can be provided with internal threads in the chamber and the front end of the stylet can constitute the second coupling element and is provided with external threads which are complementary to the internal threads and can be brought into mesh with the internal threads in response to rotation of the stylet relative to the catheter.

The electrode is preferably adjacent the front end of the aforementioned housing; as mentioned above, such electrode can constitute a corkscrew or a tip electrode. Other types of electrodes can be utilized with equal or similar advantage. The catheter further includes an elongated flexible tubular section which defines the passageway and it preferably includes a sheath made of an electrically insulating material.

The arrangement can be such that the stylet is rotatable in the passageway of the catheter in a first direction to engage the electrode with the wall of the heart (e.g., to drive the corkscrew into such wall) and in a second direction, counter to the first direction, in order to engage the second coupling element with the first coupling element, either during introduction of the front end of the stylet into the chamber or when such introduction is completed.

The distal end of the catheter can further include a drug dispenser and is then provided with at least one outlet for dispensing of one or more drugs into the wall of the heart. The drug dispenser can include the aforementioned housing of the distal end of the catheter, and the chamber in such housing then preferably constitutes a drug storing facility.

The novel features which are considered as characteristic of the invention are set forth in particular in the appended claims. The improved cardiac pacemaker lead itself, however, both as to its construction and the mode of using the same, together with additional features and advantages thereof, will be best understood upon perusal of the following detailed description of certain presently preferred specific embodiments with reference to the accompanying drawing.

BRIEF DESCRIPTION OF THE DRAWING

FIG. 2 is an enlarged sectional view of the distal end of the lead, with the front end of a first stylet inserted into the chamber of the distal end of the catheter in a position ready to anchor a corkscrew-shaped electrode into a wall of the heart;

FIG. 3 is a similar enlarged sectional view but showing a modified stylet in a first angular position (by phantom lines) ready for introduction into the chamber at the distal end of the catheter, the front end of the stylet in a different angular position being shown by solid lines;

FIG. 4 is an end elevational view of the housing of the distal end of the catheter as seen in the direction of arrow IV in FIG. 3;

DESCRIPTION OF PREFERRED EMBODIMENTS

Figure 1:
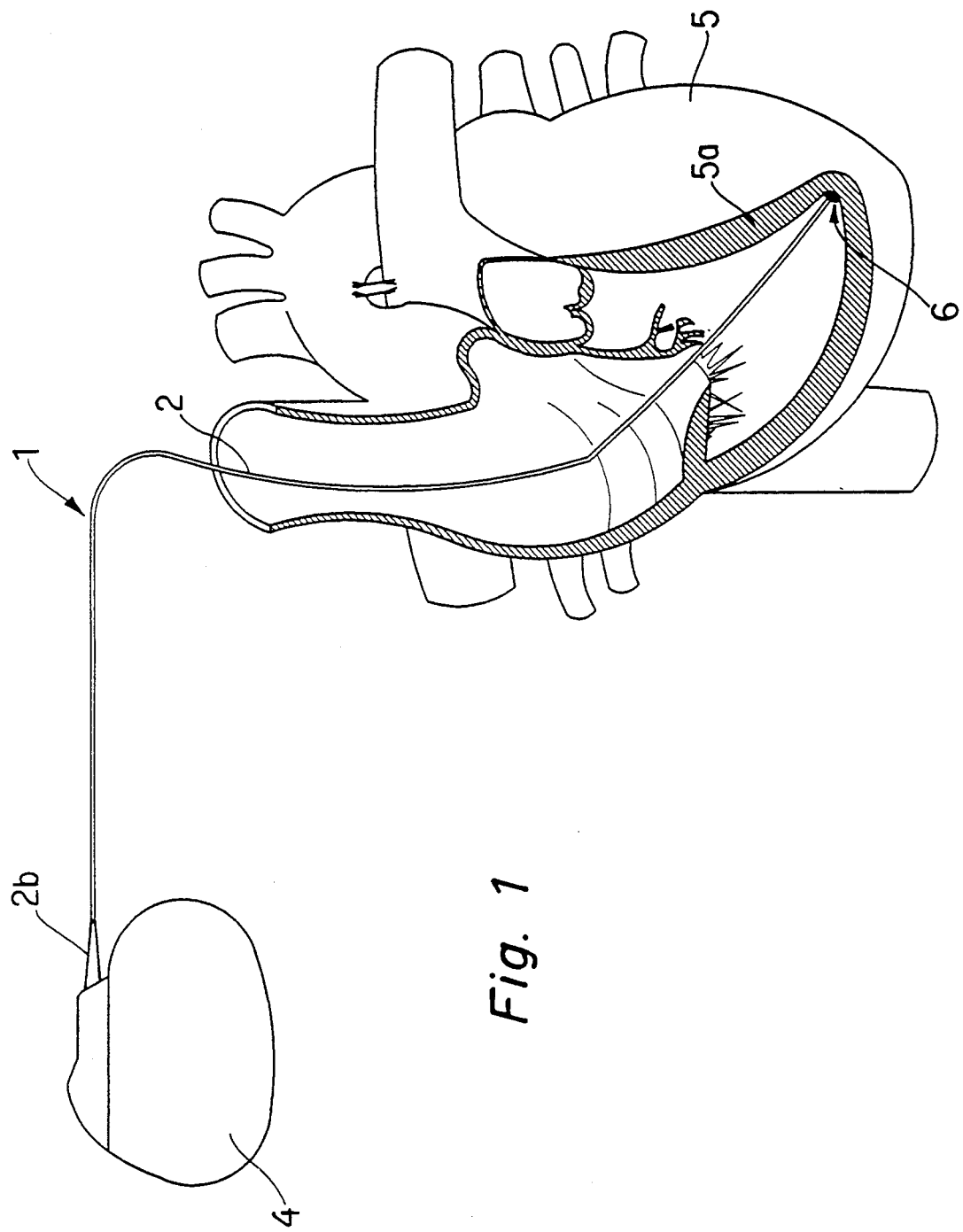
FIG. 1 is a schematic elevational view of a lead which embodies one form of the invention and extends between a cardiac pacemaker and the wall of a heart.

FIG. 1 shows a cardiac pacemaker 4, a heart 5, and a novel and improved heart lead 1 which is connected to the pacemaker 4 and has a catheter 2 including a distal end 6 with a corkscrew-shaped electrode 7 (FIGS. 2 and 3) anchored in a wall 5a of the heart 5. The major portion of the elongated flexible catheter 2 of the lead 1 is a helical wire coil 2a (FIGS. 5, 6 and 8) which defines an elongated passageway 16 extending from the proximal end 2b of the catheter to and communicating with a chamber 9 in the distal end 6. The wire coil 2a of the major portion of the catheter 2 is surrounded by an insulating sheath 3 (FIGS. 2 and 3) of suitable plastic material, and the front or foremost end of such sheath surrounds the distal end 6.

The means for extracting the distal end 6 of the catheter 2, together with the electrode 7, from the heart 5 includes an elongated flexible stylet 10 (FIG. 3) having a front portion 12 which includes or constitutes an element of an engageable coupling, and such coupling further includes a coupling element forming part of a housing 13 which, in turn, forms part of the distal end 6 and surrounds the chamber 9.

The coupling element of the housing 13 includes two eccentric projections 11 which are or can be mirror images of each other (see FIG. 4) and, in the embodiment of FIGS. 2 to 4, constitute depressed portions of the circumferential or tubular wall of the housing; such depressed portions extend into the chamber 9 behind a front wall 13a of the housing 13. The corkscrew-shaped electrode 7 is located in front of the front wall 13a and constitutes the foremost part of a helical wire 107 surrounding the housing 13 and being confined in the foremost portion of the insulating sheath 3.

FIG. 2 shows a first stylet 10A having a front end 12A insertable into the chamber 9 through the passageway 16 from the proximal end 2b of the catheter 2 and engageable with the projections 11 to thus establish a torque transmitting connection between the stylet 10A on the one hand and the housing 13 and electrode 7 on the other hand. If the stylet 10A is rotated in the clockwise direction subsequent to implantation of the distal end 6 in the heart 5 in such position that the housing wall 13a is adjacent the wall 5a of the heart, the pointed end of the electrode 7 penetrates into and is anchored in the wall 5a. However, the stylet 10A is of no assistance in extracting the distal end 6 of the catheter 2 from the heart 5; all that the front end 12A of this stylet can do is unscrew the electrode 7 from the wall 5a but it cannot assist in extracting or bring about extraction of the distal end 6 from the heart. When the stylet 10A of FIG. 2 is inserted into the distal end 6, its front end face can move axially all the way into abutment with the inner side of the wall 13a. At such time, the coupling element 12A is in torque transmitting engagement with the projections 11 of the housing 13.

The stylet 10 of FIG. 3 is constructed and dimensioned in accordance with a feature of the present invention. The housing 13 of the distal end 6 of the catheter 2 is or can be identical with the housing 13 of FIG. 2. The coupling element 12 of the stylet 10 is shorter than the coupling element 12A, and its length is selected in such a way that the entire element 12 is located in front of the projections 11 when the front end face of the stylet 10 abuts the inner side of the wall 13a. If the coupling element 12 is only partially inserted into the chamber 9 of the housing 13 which is shown in FIG. 3, or the stylet 10 is replaced with the stylet 10A, the stylet 10 or 10A can be used as a means for rotating the housing 13 in a direction to anchor the electrode 7 in, or to unscrew the electrode 7 from, the wall 5a of the heart 5. However, the stylet 10 of FIG. 3 can also be used to extract the housing 13 and the electrode 7 from the heart 5. All that is necessary is to move the stylet 10 axially or lengthwise through the passageway 16 and into the chamber 9 so that the coupling element 12 advances beyond the projections 11. Such insertion of the coupling element 12 into the chamber 9 is possible in one or more (e.g., two) first angular positions of the stylet 10. The stylet 10 is then turned relative to the catheter 2 to one of a preferably infinite number of second angular positions (e.g., to a second position substantially at right angles to a first angular position) whereby the portions 12a, 12b of the coupling element 12 are at least partially aligned with the projections 11 and can cooperate with these projections in order to extract the distal end 6 from the heart 5 in response to a pull upon that (proximal) end of the stylet 10 which is accessible at the proximal end 2b of the catheter 2. The arrangement is or can be such that the stylet 10A or 10 is used to first unscrew the electrode 7 from the wall 5a and the stylet 10 is thereupon used to extract the distal end 6 from the heart. The person in charge of extracting the distal end 6 realizes that the stylet 10 is fully inserted into the chamber 9 when the front end of this stylet strikes the wall 13a.

An advantage of the novel extracting means including the coupling element (11+11) of the distal end 6 and the coupling element 12 of the stylet 10 is that the force which is needed to extract the distal end 6 from the heart 5 can be applied directly to the distal end (i.e., to the housing 13 of the distal end) rather than to the wire coil 2a of the catheter 2. This greatly reduces the likelihood of tearing of the catheter 2 or of separation of wire coil 2a of the catheter from the distal end 6 which could necessitate open heart surgery in order to gain access to and to remove the distal end 6 and its electrode 7 from the heart.

The configuration of the coupling element 12 can be selected in such a way that turning of the stylet 10 in a first direction (e.g., clockwise, as viewed in FIG. 3) results in implantation of the electrode 7 in the wall 5a and turning of the stylet 10 in a second direction counter to the first direction results in requisite alignment of the coupling elements 12 and 11, 11 preparatory to extraction of the distal end 6 of the catheter 2 from the heart 5.

An advantage of the coupling of FIGS. 3 and 4 is that it can be produced at a reasonable cost. All that is necessary is to provide the housing 13 with one or more projections 11 or with an otherwise configured coupling element and to provide the front end (coupling element 12) of the stylet 10 with one or more flats which ensure that the substantially hammerhead-shaped or like part 12 can bypass the projection or projections 11 in at least one first angular position of the stylet 10 but that the part 12 is at least partially aligned with the projection or projections 11 in at least one second angular position of the stylet 10 so that extraction of the stylet from the body of the patient invariably involves extraction of the distal end 6 and its electrode 7 without any stressing of the connection between the distal end and the wire coil 2a of the catheter 2 as well as without any stressing of the wire coil 2a. This practically eliminates the need for open heart surgery due to unintentional breakage or tearing of the catheter 2, either in the region of its wire coil 2a or in the region of connection of the wire coil 2a to the distal end 6.

The housing 13 constitutes a desirable and advantageous feature of the distal end 6. Thus, such housing defines the chamber 9 and carries the helical wire 107 including the electrode 7. In addition, the housing 13 is provided with the coupling element including the projections 11 and, furthermore, this housing can serve as a sturdy anvil or abutment for the stylet 10A or 10 during implantation of the lead 1 in the body of a patient. Moreover, the housing 13 can constitute a sturdy and reliable device for transmission of torque from the stylet 10A or 10 to the helical wire 107 during anchoring of the electrode 7 in the wall 5a. Still further, the illustrated housing 13 can be reliably affixed to the front end of the sheath 3 as well as to the front end of the wire coil 2a of the catheter 2. In addition, the housing 13 can serve as a means for transmitting stimuli from the wire coil 2a to the electrode 7 and hence to a selected portion of the heart 5.

An advantage of the feature that engagement of the coupling element 12 with the coupling element including the projections 11 necessitates rotation of the stylet 10 in a first direction whereas anchoring of the electrode 7 in the wall 5a necessitates rotation of the stylet 10 in the opposite direction is that the electrode 7 is automatically withdrawn from the wall 5a as a result of proper alignment of the coupling element 12 with the projections 11 preparatory to extraction of the distal end 6 and of its electrode 7 from the heart 5. This holds especially true if the electrode 7 is not strongly anchored in the tissue of the wall 5a.

Figure 5:
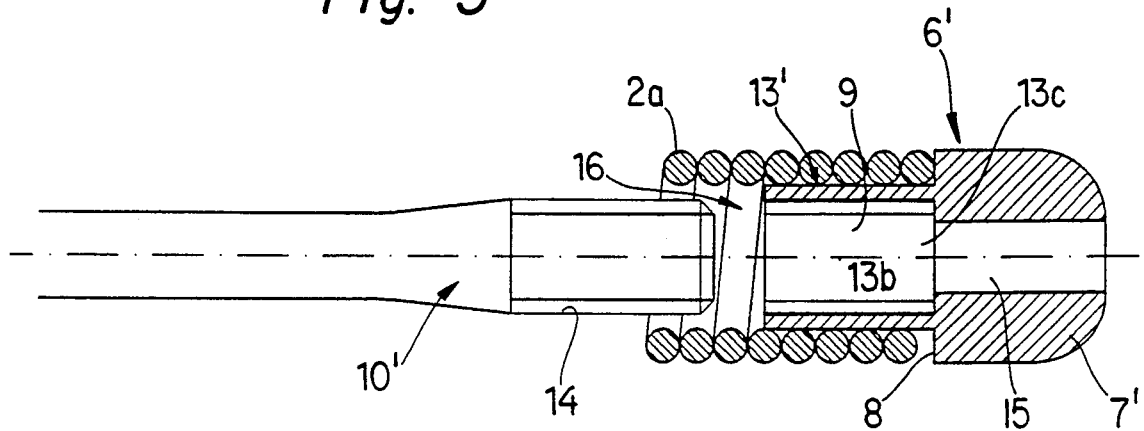
FIG. 5 is a view similar to that of FIGS. 2 or 3 but showing a modified distal end and a modified stylet in a position in which the coupling element of the stylet is spaced apart from the coupling element of the distal end of the catheter.
Figure 6:
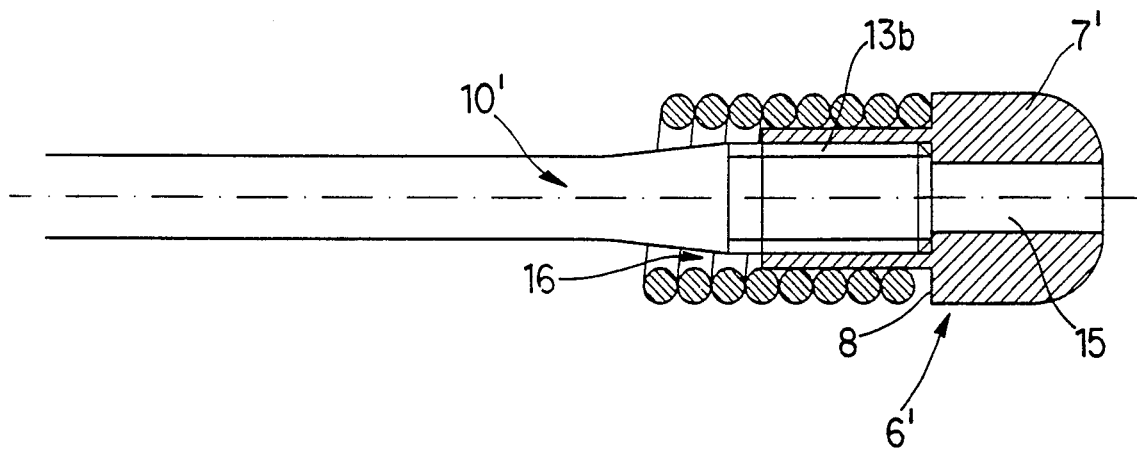
FIG. 6 shows the structure of FIG. 5 but with the coupling in engaged condition.

FIGS. 5 and 6 show a portion of a modified lead wherein the coupling element 14 at the front end of the stylet 10' includes an external thread movable into mesh with the internal thread 13b of a housing 13' which includes an integral tip electrode 7'. The latter can be provided with a shoulder 8 to ensure more reliable anchoring in a wall of the heart. The internal thread 13b constitutes a coupling element which is complementary to the external thread of the coupling element 14. The stylet 10' of FIGS. 5 and 6 is rotatable in the passageway 16 of the wire coil 2a of the catheter 2 so that the coupling element 14 can be brought into mesh with the coupling element including the internal thread 13b in the chamber 9. At such time (see FIG. 6), the stylet 10' of FIGS. 5 and 6 is ready to extract the distal end 6' from the heart. The internal thread 13b can be provided in a sleeve 13c which is a press fit in and can be considered an integral part of the housing 13'.

The coupling including the elements 13b, 14 is designed in such a way that the stylet 10' can be rotated through 360°, less than 360° or several times 360° preparatory to extraction of the distal end 6' and electrode 7' from the heart.

Figure 7:
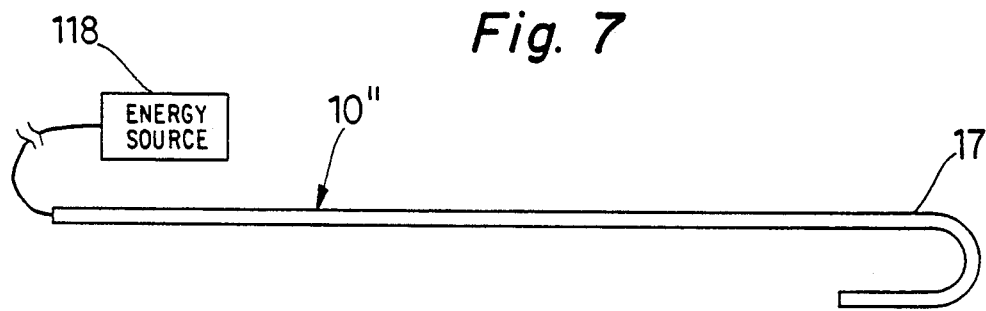
FIG. 7 is an elevational view of the front end of a further stylet.
Figure 7A:
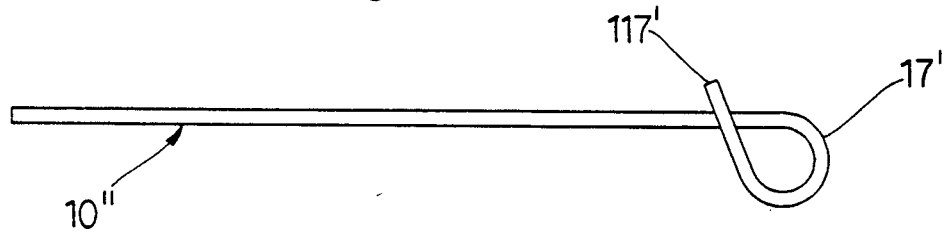
FIG. 7a shows the stylet of FIG. 7 but with the coupling element of the stylet in condition ready for engagement with the complementary coupling element at the distal end of the catheter.

FIGS. 7 and 7a show a further stylet 10" wherein the front end 17 is made of or contains a memory metal, i.e., a metallic substance which causes deformation of the front end 17 in response to a temperature change. Such front end 17 constitutes a coupling element whose configuration is changed from that (substantially U-shaped) which is shown in FIG. 7 to the substantially loop-shaped configuration 17' of FIG. 7a in response to a change of temperature, for example, in response to heating by body heat upon introduction into the chamber 9 of the distal end 6' shown in FIG. 8 or as a result of heating by a discrete temperature changing means. The temperature changing means can include a source 18 of electrical energy which is connected to the coupling element or front end 17 by a conductor constituting the major part of the wire-like flexible stylet 10".

Figure 8:
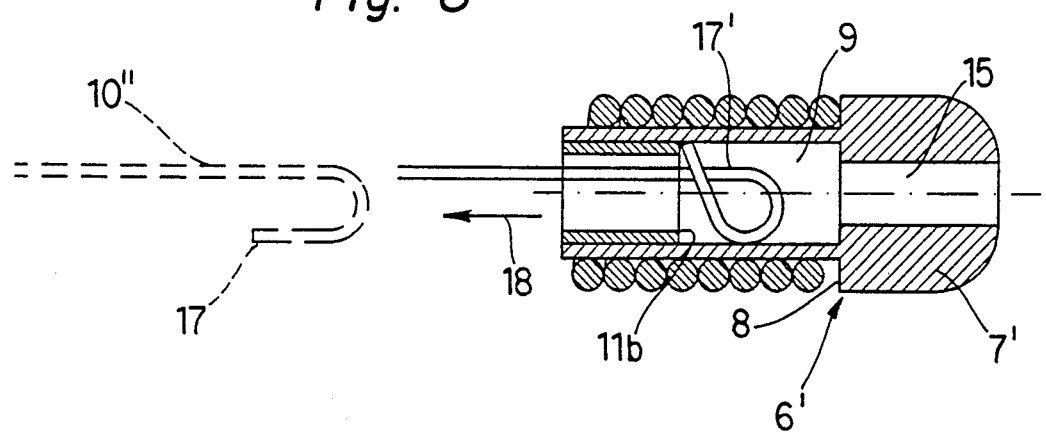
FIG. 8 is an elevational view of the front end of the stylet of FIGS. 7 and 7a and a sectional view of the associated distal end of a catheter, the coupling element of the stylet being shown by solid lines in the chamber of the distal end of the catheter and by broken lines prior to its deformation in response to heating.

The coupling element which is complementary to the deformable coupling element 17 includes an undercut portion here shown as an annular shoulder 11b in the chamber 9, and such undercut portion or shoulder is engaged by the free end 117' of the deformed coupling element 17' to thus ensure that the stylet 10" can extract the distal end 6' from the heart in response to exertion of a pull in the direction of arrow 18 as soon as the tip 117' engages the shoulder 11b in the chamber 9 of the distal end 6' of FIG. 8. If desired, the entire stylet 10" can be made of memory metal.

The couplings which are shown in FIGS. 5-6 and 7-8 exhibit the same advantages as the coupling 11, 12 of FIGS. 3 and 4, i.e., such couplings can establish a reliable form-locking connection between the stylet 10' or 10" and the distal end 6' to thus ensure predictable extraction of the distal end 6' from the heart. In each instance, the force which is required to extract the distal end 6 or 6' is applied directly to, or at least in immediate proximity to, the distal end 6 or 6' so as to ensure that the distal end is invariably extracted in response to extraction of the stylet 10, 10' or 10" from the body of a patient.

The housing 13 or 13' performs several important and desirable functions, i.e., this housing carries the electrode 7 or 7a and such housing also serves to define the chamber 9 for the front end of the stylet 10, 10' or 10". Still further, and as actually shown in FIGS. 3, 4, 5, 6 and 8, the housing 13 or 13' can confine the coupling element 11, 11 or 13b or 11b of the catheter 2. In accordance with an additional feature of the invention, the housing 13 or 13' can also serve or include or carry a drug dispenser which can discharge metered quantities of one or more drugs into the tissue of the wall 5a when the distal end 6 or 6' is properly implanted in the heart 5. FIGS. 5, 6 and 8 show that the tip electrode 7' of the housing 13' has an outlet 15 in the form of an axially extending bore or hole which can discharge one or more drugs toward the tissue of the wall 5a when the electrode 7' contacts the wall 5a. The chamber 9 can perform the additional function of serving as a drug storing facility. For example, the drug or drugs which are dispensed into the tissue of the wall 5a can serve to counter thrombus formation, fibrosis, inflammation or arrythmias. Fresh drug or drugs can be admitted into the chamber 9 through the passageway 16. FIG. 3 shows that the front wall 13a of the housing 13 can also include an outlet 115 (e.g., an outlet smaller than the bore or hole 15) for controlled (gradual) dispensing of one or more drugs into the wall 5a.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A lead for connecting a cardiac pacemaker with a wall of a heart, comprising an elongated flexible tubular catheter having a distal end including an electrode engageable with the wall upon implantation of said distal end into the heart, said catheter having a chamber at said distal end and defining an elongated passageway communicating with said chamber; and means for extracting said distal end from the heart, including an elongated stylet having a front end insertable into said chamber through said passageway, and an engageable coupling including a first coupling element provided in said catheter at said chamber and a second coupling element provided on said stylet at said front end and engageable with said first coupling element on insertion of said front end into said chamber, said second coupling element containing memory metal and being deformable in response to temperature changes upon insertion of the front end of said stylet into said chamber to thereby engage said first coupling element.

2. The lead of claim 1, wherein said catheter has a proximal end and said passageway has an inlet at said proximal end for the front end of said stylet.

3. The lead of claim 1, wherein one of said coupling elements comprises at least one projection.

4. The lead of claim 1, wherein said first coupling element includes an annular shoulder in said chamber.

5. The lead of claim 1, further comprising means for changing the temperature of said second coupling element.

6. The lead of claim 5, wherein said temperature changing means includes a source of electrical energy and said stylet comprises a conductor which connects said energy source with said second coupling element.

7. The lead of claim 1, wherein said distal end includes a housing which surrounds said chamber and includes a front portion, said electrode being adjacent said front portion.

8. The lead of claim 7, wherein said electrode is a tip electrode.

9. The lead of claim 7, wherein said catheter further includes an elongated tubular section and a sheath which consists, at least in part, of an electrically insulating material.

10. The lead of claim 1, wherein said distal end includes a drug dispenser and has at least one outlet for dispensing a drug into the wall.

11. The lead of claim 10, wherein said drug dispenser includes a housing which surrounds said chamber and said chamber constitutes a drug storing facility.

* * * * *